(12) United States Patent
Wong et al.

(10) Patent No.: US 7,684,610 B2
(45) Date of Patent: *Mar. 23, 2010

(54) ROTATING PRISM COMPONENT INSPECTION SYSTEM

(75) Inventors: Soon Wei Wong, Singapore (SG); Victor Vertoprakhov, NovosiBirsk (RU); WenSen Zhou, Singapore (SG); Ashedah Binti Jusoh Noor, Singapore (SG); Tian Poh Yew, Singapore (SG); Kundapura Paremeshwara Srinivas, Singapore (SG)

(73) Assignee: Microview Technologies PTE Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/072,468

(22) Filed: Feb. 26, 2008

(65) Prior Publication Data

US 2008/0152211 A1    Jun. 26, 2008

Related U.S. Application Data

(63) Continuation of application No. 10/653,825, filed on Sep. 3, 2003, now Pat. No. 7,340,085.

(51) Int. Cl.
*G06K 9/00* (2006.01)
*G02B 5/04* (2006.01)

(52) U.S. Cl. .................. 382/141; 382/145; 359/831

(58) Field of Classification Search ............ 382/141, 382/146, 145; 356/237.1, 431, 237.5, 28; 359/363, 618, 629, 375, 556, 638, 837, 834, 359/798, 431, 726, 589, 569, 401, 831; 349/5, 349/8; 348/757, 126
See application file for complete search history.

(56) References Cited

U.S. PATENT DOCUMENTS

| | | | |
|---|---|---|---|
| 3,283,898 A | 11/1966 | Calhoun | |
| 4,040,748 A | 8/1977 | Belleson et al. | |
| 4,148,065 A | 4/1979 | Nakagawa et al. | |
| 4,593,406 A | 6/1986 | Stone | |
| 5,212,647 A | 5/1993 | Raney et al. | |
| 5,430,666 A | 7/1995 | DeAngelis et al. | |
| 5,677,763 A * | 10/1997 | Redmond | 356/73 |
| 6,055,054 A | 4/2000 | Beaty et al. | |
| 6,278,797 B1 | 8/2001 | Nagasaki et al. | |
| 6,307,210 B1 | 10/2001 | Suzuki et al. | |

(Continued)

OTHER PUBLICATIONS

Search Report for PCT/IB2004/002868 dated Jan. 3, 2005 in co-pending PCT filing of parent U.S. application (4 pgs.).

(Continued)

*Primary Examiner*—Sheela C Chawan
(74) *Attorney, Agent, or Firm*—Jackson Walker L.L.P.; Christopher J. Rourk

(57) ABSTRACT

An inspection system is provided. The system includes a rotating prism having a first end and a second end. The first end receives a first image area, such as a circular view, and rotates about a center point so as to cover a field of view area that is larger than the first image area, such as a larger circle that is defined by the smaller circle of view as it rotates around the center point. The second end remains centered on the center point and provides a viewing area that does not change in dimension. An image data system at the second end of the rotating prism generates image data as the prism rotates so as to generate two or more sets of image data that are contained within the field of view area.

19 Claims, 5 Drawing Sheets

U.S. PATENT DOCUMENTS

| | | | |
|---|---|---|---|
| 6,567,161 B1 * | 5/2003 | Lee | 356/237.1 |
| 6,721,033 B1 | 4/2004 | Kaneko | |
| 7,022,986 B2 | 4/2006 | Shinada et al. | |
| 7,113,629 B2 | 9/2006 | Onishi | |
| 7,340,085 B2 * | 3/2008 | Wong et al. | 382/141 |
| 2002/0150286 A1 | 10/2002 | Onishi | |

OTHER PUBLICATIONS

Search Report for PCT/IB2004/002868 dated Jan. 3, 2005.

* cited by examiner

ROTATING PRISM COMPONENT INSPECTION SYSTEM

CROSS-REFERENCE TO RELATED APPLICATIONS

This application is a continuation application of U.S. patent application Ser. No. 10/653,825, filed Sep. 3, 2003 now U.S. Pat. No. 7,340,085, entitled "Rotating Prism Component Inspection System."

FIELD OF THE INVENTION

The present invention pertains to the field of inspection systems, and more particularly to a system and method for inspecting semiconductor devices that uses a rotating prism or other suitable devices to provide a changing view to a fixed view area.

BACKGROUND

Component inspection systems are known in the art. Such component inspection systems use component image data to perform component inspection. The component image data can be analyzed using a variety of techniques to determine whether the component is acceptable or unacceptable.

One requirement for such component inspection systems is that the pixel density for image data that is used to inspect the component must have a high enough resolution to identify non-conforming conditions. For example, if a potential defect is one micron in diameter, then the pixel resolution must be less than one micron in order to generate image data having a sufficient resolution to identify and analyze the defect. In order to obtain a sufficient level of resolution, it is common to move the camera or component that is being inspected, so as to cover two or more sections of the component. However, moving the component or camera is time consuming, and slows the inspection process.

SUMMARY OF THE INVENTION

In accordance with the present invention, a system and method for component inspection are provided that overcome known problems with component inspection systems and methods.

In particular, a system and method for component inspection are provided that use a rotating prism to provide a changing view to a camera, so as to allow the image data device to generate a higher resolution image of the component without the need for moving the camera or component.

In accordance with an exemplary embodiment of the present invention, a system for inspecting a component is provided. The system includes a rotating prism having a first end and a second end. The first end receives a first image area, such as a circular view, and rotates about a center point so as to cover a field of view area that is larger than the first image area, such as a larger circle that is defined by the smaller circle of view as it rotates around the center point. The second end remains centered on the center point and provides a viewing area that does not change in dimension. An image data system at the second end of the rotating prism generates image data as the prism rotates so as to generate two or more sets of image data that are contained within the field of view area.

The present invention provides many important technical advantages. One important technical advantage of the present invention is a system and method for inspecting components that utilizes a rotating prism or other suitable devices to allow a component to be inspected by gathering a number of image data sets, where each image data set is generated when the prism is at a different angular position. In this manner, multiple detail images of the component can be generated without moving the component or camera.

Those skilled in the art will further appreciate the advantages and superior features of the invention together with other important aspects thereof on reading the detailed description that follows in conjunction with the drawings.

DETAILED DESCRIPTION OF PREFERRED EMBODIMENTS

Figure 1A:
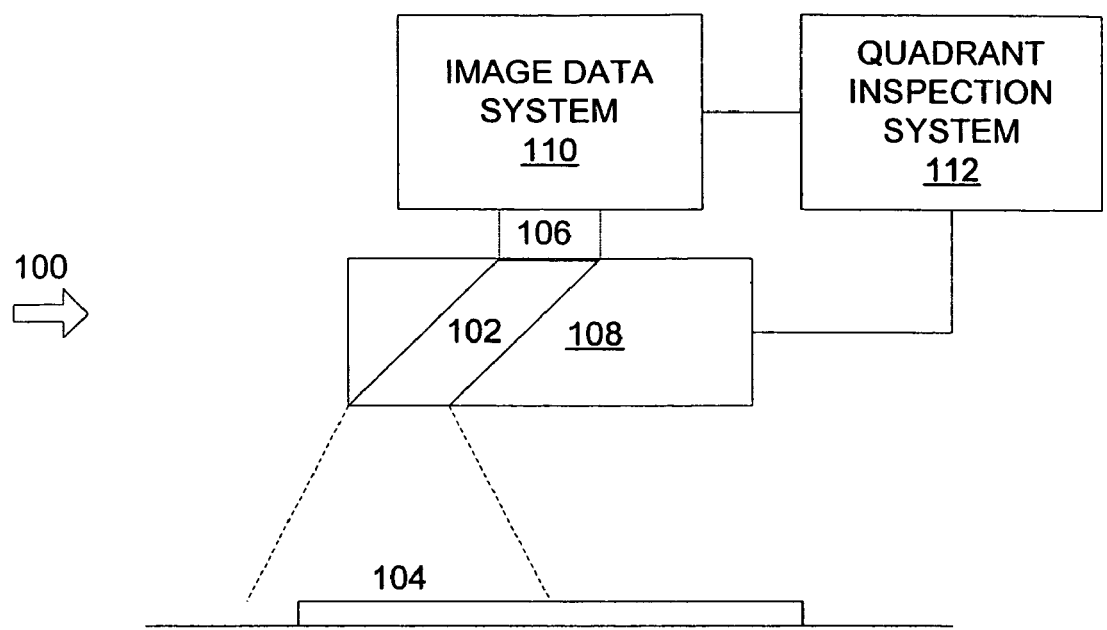
FIG. 1A is a diagram of system for performing an inspection in accordance with an exemplary embodiment of the present invention.

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

FIG. 1A is a diagram of system 100 for performing an inspection in accordance with an exemplary embodiment of the present invention. System 100 uses a rotating prism to generate image data over a field of view that is larger than a field of view of a camera, so as to allow components to be inspected without moving the component or the camera.

System 100 includes rotating prism 102. Rotating prism 102 can be used to transfer an image from an image area 104 to a viewing area 106. Thus, a viewer at viewing area 106 will see an image of what is contained within image area 104, where this image can change as rotating prism 102 rotates. It is noted that a viewer at image area 104 would be able to observe viewing area 106 through rotating prism 102, but that this view would only be that of a rotating viewing area 106. In this manner, a field of view can be encompassed at viewing area 106 by rotating prism 102 that is larger than the field of view that can be directly covered by viewing area 106 without the aid of rotating prism 102.

For example, image data system 110 can be used to directly generate image data for component inspection or for other suitable purposes. In this exemplary embodiment, component inspection can be performed by determining the pixel density required to inspect features of the component, such as by determining the area that must be covered by each pixel in order to provide the required level of detail for recognition of damage or other conditions. If the number of pixels required to inspect an entire component is greater than the number of pixels generated by image data system 110 at the desired level of detail, it would be necessary to move the component or image data system 110 in order to generate image data of the entire component. Rotating prism 102 can be used to provide the image data of the entire component to image data system 110 without moving either image data system 110 or the component. In this manner, rotating prism 102 is rotated about an axis such that viewing area 106 remains in the field of view of image data system 110 but image area 104 rotates around and covers an area or field of view that encompasses the entire component.

Rotating prism 102 includes prism rotation system 108. Prism rotation system 108 can be disposed about rotating prism 102, can be the device that holds rotating prism 102, can include motors or other motive devices, lighting elements, and other suitable components. Prism rotation system 108 is coupled to quadrant inspection system 112, which is also coupled to image data system 110. Quadrant inspection system 112 and image data system 110 can be implemented in hardware, software, or a suitable combination of hardware and software, and can be one or more software systems operating on a general purpose processing platform. As used herein, a hardware system can include discrete semiconductor devices, an application-specific integrated circuit, a field programmable gate array or other suitable devices. A software system can include one or more objects, agents, threads, lines of code, subroutines, separate software applications, user-readable (source) code, machine-readable (object) code, two or more lines of code in two or more corresponding software applications, databases, or other suitable software architectures. In one exemplary embodiment, a software system can include one or more lines of code in a general purpose software application, such as an operating system, and one or more lines of code in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. In one exemplary embodiment, systems and components are coupled to other systems and components through intervening systems and components, such as through an operating system.

Image data system 110 generates image data for an area that corresponds to viewing area 106. In one exemplary embodiment, image data system 110 can include one or more lenses, picture element (pixel) arrays, and other suitable image data generation components. For example, image data system 110 can generate a 1024×1024 pixel array or suitable arrays for capturing the image presented in viewing area 106.

Quadrant inspection system 112 controls the generation of image data by image data system 110 and the rotation speed of prism rotation system 108. In this manner, image data system 110 can be used to capture image data from a suitable number of areas that encompass the entire component being inspected. Depending on the field of view and the image area 104, one or more components could be inspected using system 100, such as where a first component is encompassed by the first half of the field of view, and a second component is encompassed by a second half of the field of view, where a component lies within each quadrant of the field of view, or in other suitable configurations.

Quadrant inspection system 112 can also accommodate for the angular displacement of image data generated by image data system 110. For example, features in the image data generated when rotating prism 102 is in a first position may have an angular displacement relative to features in image data that is generated when rotating prism 102 is a second position. If rotating prism 102 is generating image data of quadrants of a die having straight rows of features that are being inspected, then the angular orientation of the features in the first quadrant image data can be 90 degrees displaced from the angular orientation of the features in the second quadrant image data. Quadrant inspection system 112 can rotate the image data, rotate the analysis frame, or otherwise compensate for changes in the angular orientation of data sets, so as to allow inspection of image data from different sections of the field of view to be performed irrespective of the angular orientation of features in such sections relative to features in other sections.

Figure 1B:
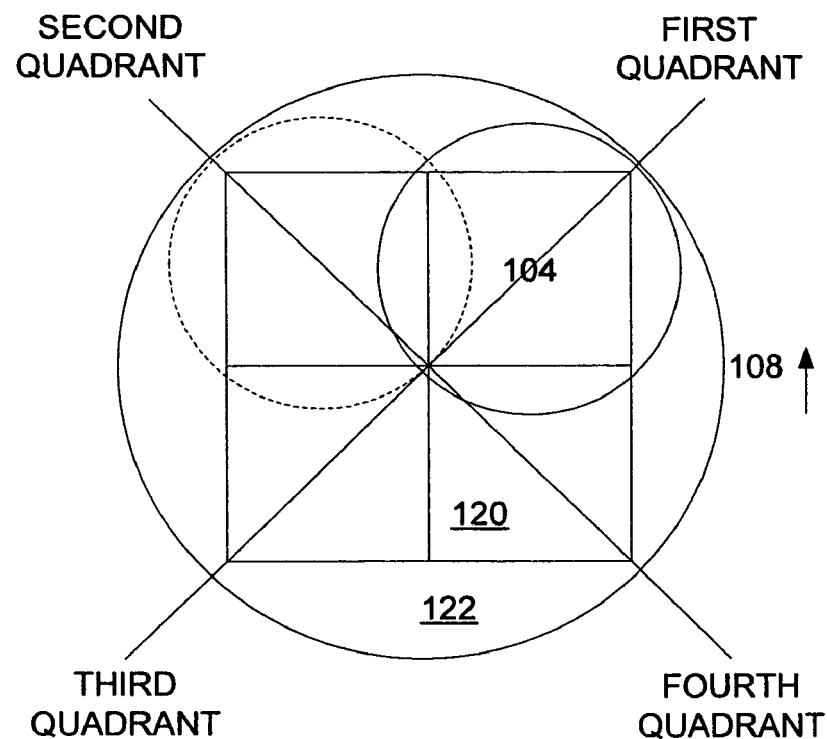
FIG. 1B is a diagram of a component in a field of view in accordance with an exemplary embodiment of the present invention.

FIG. 1B is a diagram of a component 120 in a field of view 122 in accordance with an exemplary embodiment of the present invention. Component 120 can be encompassed by field of view 122 by rotating image area 104 about axis 124. If prism rotation system 108 is rotated in the direction of the arrow in FIG. 1B, then first quadrant image data, second quadrant image data, third quadrant image data, and fourth quadrant image data can be generated that correspond to quadrants of semiconductor die 120. Likewise, areas outside of semiconductor die 120 can also be encompassed, such that multiple semiconductor dies could be encompassed where the dies are small enough to fit within areas that fall outside of semiconductor die 120. In this exemplary embodiment, system 100 can be used to perform inspection of all dies cut from a wafer, or other suitable components.

Figure 1C:
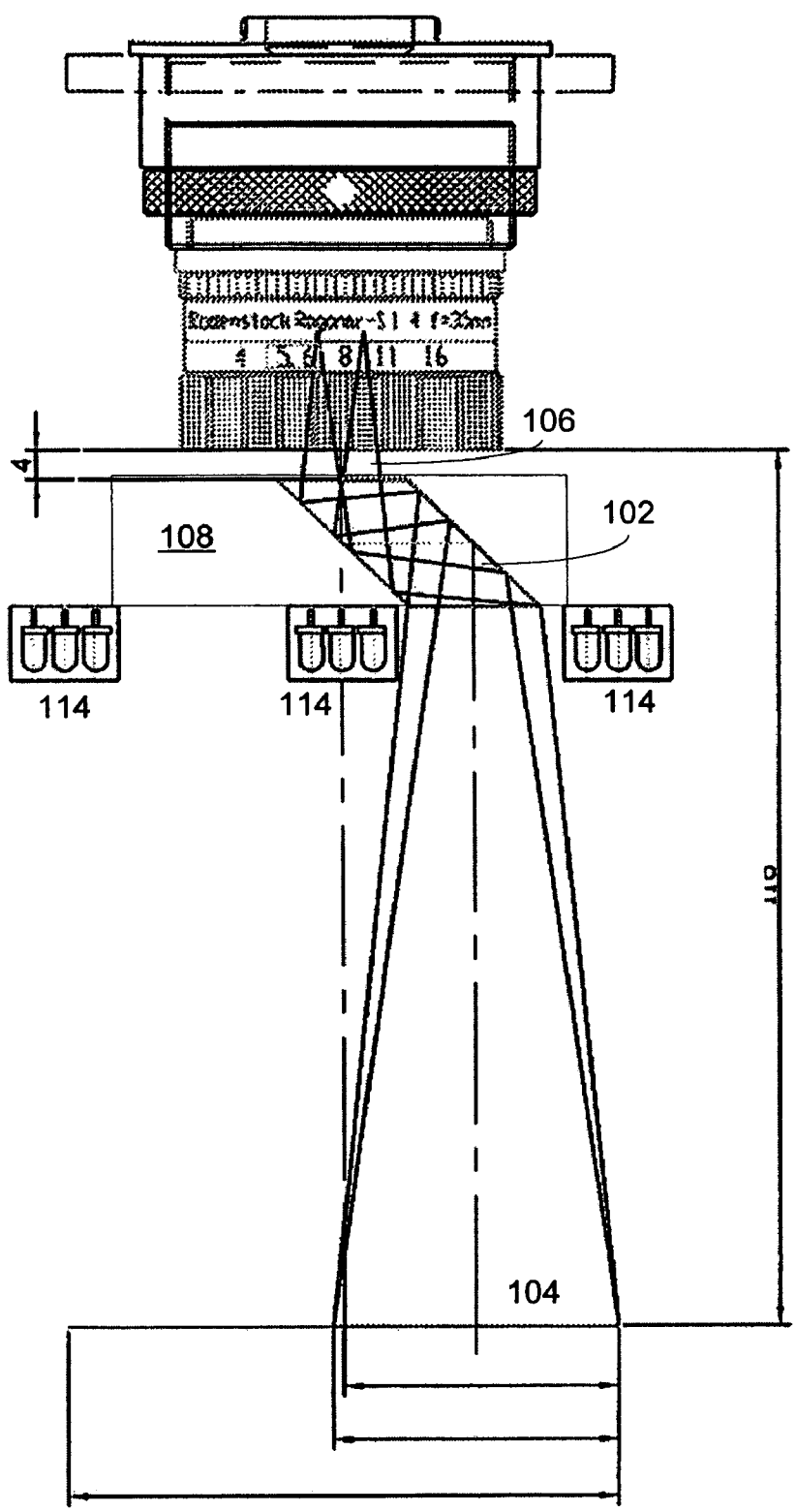
FIG. 1C is a diagram of a lens apparatus that is used to focus image data at viewing area.

FIG. 1C is a diagram of a lens apparatus 126 that is used to focus image data at viewing area 106. Light array 114 is shown disposed on prism rotation system 108, such that the lighting generated in image area 104 remains uniform regardless of the angle of rotation of prism rotation system 108. As shown, rotating prism 102 reflects light from image area 104, such that the field of view seen from viewing area 106 encompasses the entire field view, whereas the image area seen from image area 104 encompasses the focal point of lens apparatus 126.

Figure 1D:
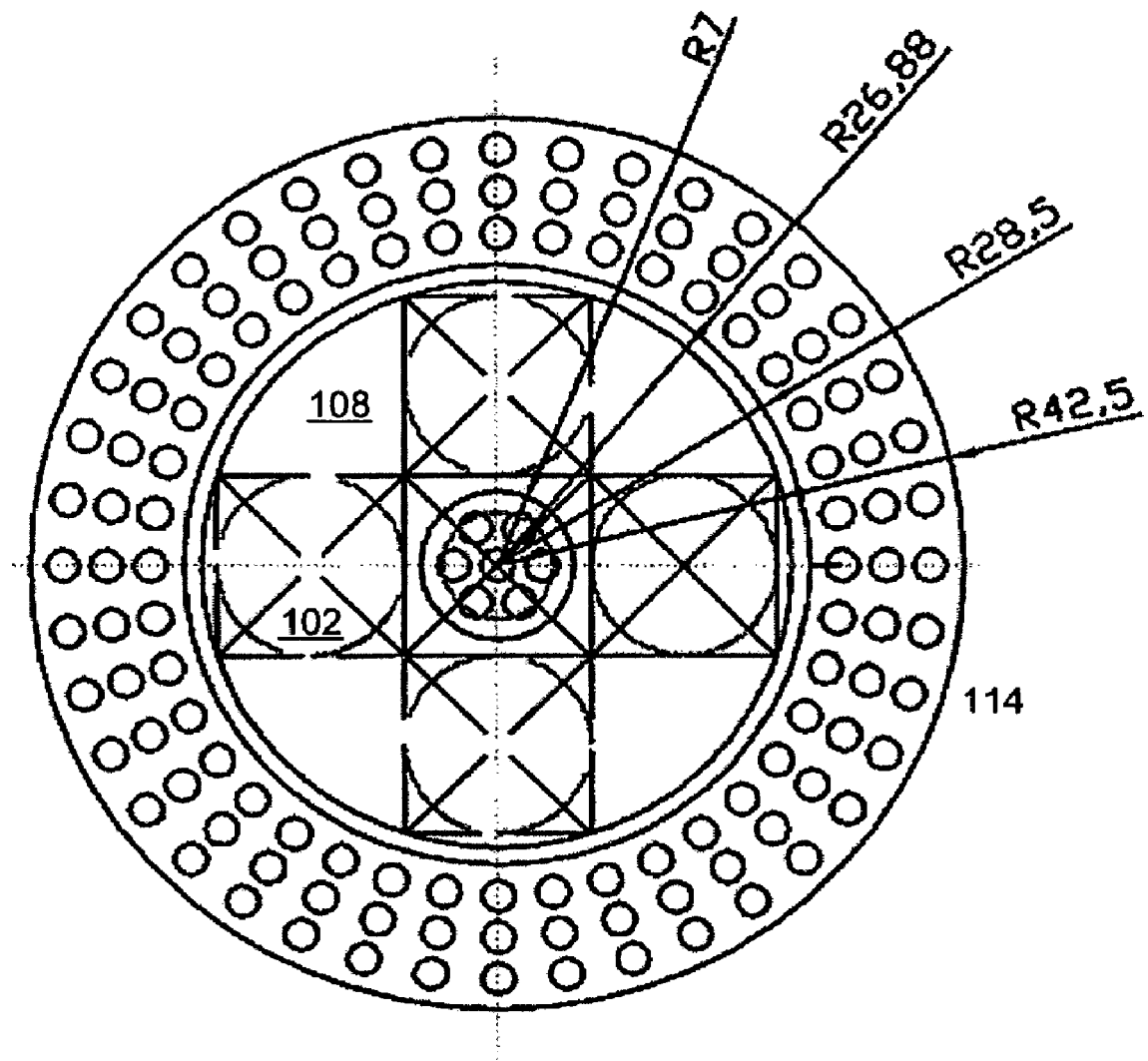
FIG. 1D is a diagram of a light array disposed about a prism rotation system for a rotating prism.

FIG. 1D is a diagram of a light array 114 disposed about a prism rotation system 108 for rotating prism 102. As shown, light array 114 can include a partial array of LED Lights or other suitable lights that are used to maintain a constant lighting pattern regardless of the angle of orientation for prism rotation system 108 or rotating prism 102.

In operation, system 100 is used to perform inspection of one or more components. System 100 allows pixel densities to be obtained by using a rotating prism in a manner that allows an entire field of view to be inspected without moving the image data system or component. Likewise, multiple components can be inspected, such as dies cut from a semiconductor wafer, or other suitable inspections can be performed so as to avoid movement of an image data system or component.

Figure 2:
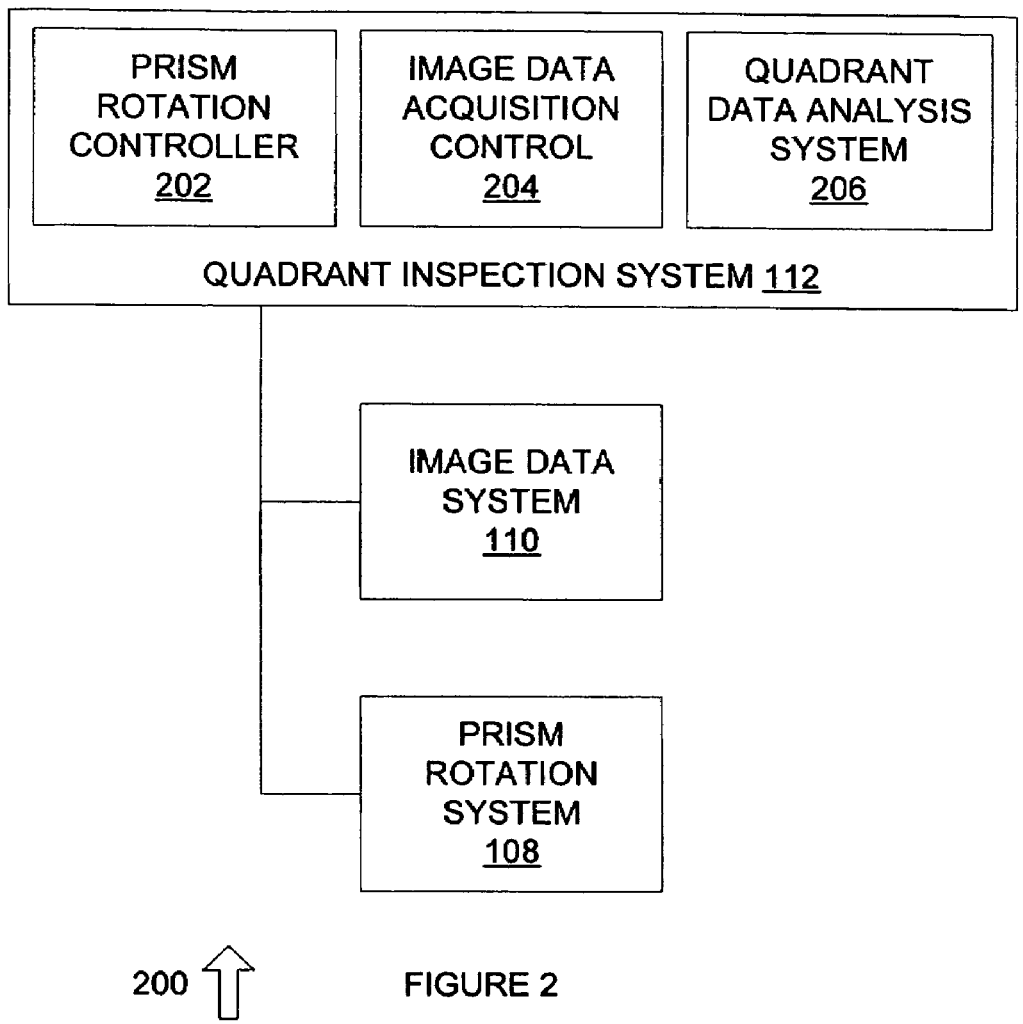
FIG. 2 is a diagram of a system for inspecting components in accordance with an exemplary embodiment of the present invention.

FIG. 2 is a diagram of a system 200 for inspecting components in accordance with an exemplary embodiment of the present invention. System 200 includes prism rotation system 108, image data system 110, quadrant inspection system 112, prism rotation controller 202, image data acquisition control 204, and quadrant data analysis system 206, each of which can be implemented in hardware, software, or a suitable combination of hardware and software, and which can be one or more software systems operating on a general purpose processing platform.

Prism rotation controller 202 controls the speed of rotation for a rotating prism 102 in conjunction with prism rotation system 108. In one exemplary embodiment, prism rotation system 108 includes a support and associated motors or other motive devices that are used to control an angle of rotation or speed of rotation of a rotating prism. Prism rotation controller 202 can adjust the speed of rotation so as to correspond to an image data system 110 frame generation rate or other suitable factors.

Image data acquisition control 204 controls image data system 110 to generate image data at a rate that corresponds to the rate of rotation of prism rotation system 108. In one exemplary embodiment, image data can be generated for quadrants, or for other suitable areas, such that image data acquisition control 204 causes an image data system 110 to capture image data presently in an area encompassed by viewing area 104. Image data acquisition control 204 receives prism rotation rate data from prism rotation controller 202, so as to ensure that the image data is generated in synchronization with the rotation of rotating prism 102.

Quadrant data analysis system 206 receives the image data generated by image data system 110 and performs quadrant analysis on the data. In one exemplary embodiment, quadrant data analysis system 206 can also perform area analysis for areas corresponding to one-third of the circular field of view, one-fifth of the circular field of view, or the suitable areas. Quadrant data analysis system 206 can identify features or items within a die or component, and can compensate for the degree or angle of rotation from a reference point. In one exemplary embodiment, quadrant data analysis system 206 can identify such features in a component image data set without rotating the image set, can compensate the image data set for angular rotation, or can perform other suitable functions.

In operation, system 200 allows a component such as a semiconductor die to be inspected where the level of detail that is required would otherwise require the die to be moved or the image data generation system to be moved to generate image data for the entire component. System 200 controls a rotating prism in a manner that image data for the entire component can be generated without moving the image data generation system or the component, and further allows for angles of rotation to be compensated for, either by rotating the image data, rotating the inspection frame, identifying components or features of the image data regardless of the angle of orientation, or in other suitable manners.

Figure 3:
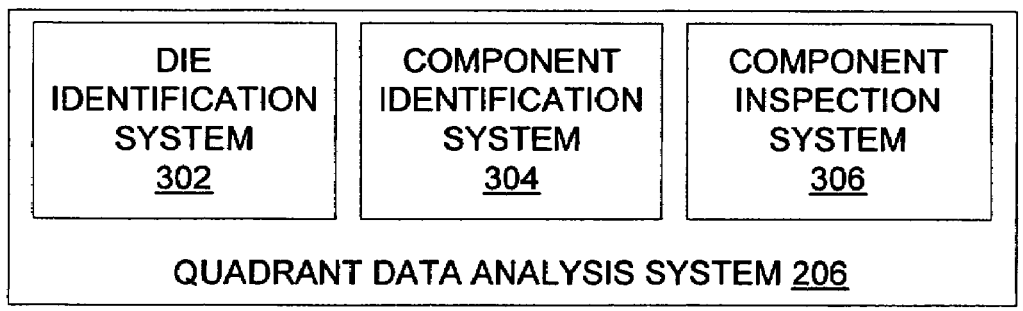
FIG. 3 is a diagram of system for quadrant data analysis in accordance with an exemplary embodiment of the present invention.

FIG. 3 is a diagram of system 300 for quadrant data analysis in accordance with an exemplary embodiment of the present invention. System 300 includes quadrant data analysis system 206 and die identification system 302, feature identification system 304, and feature inspection system 306, each of which can be implemented in hardware, software, or suitable combination of hardware and software, and which can be one or more software systems operating on a general purpose processing platform.

Die identification system 302 identifies one or more die quadrants or other die features from image data. In one exemplary embodiment, a semiconductor die can be inspected such that the known dimensions, angular orientation, size of the die, and features on the die can be used to determine the angular orientation of the die in a set of image data. Die identification system 302 thus allows quadrants or other sections of the die to be identified based on die perimeter data or other suitable data.

Feature identification system 304 identifies one or more features within a set of image data. In one exemplary embodiment, feature identification system 304 can be used in conjunction with die identification system 302, such as where feature locations are known relative to die perimeter data, die quadrant data, or other suitable data. Likewise, feature identification system 304 can locate features in sets of image data without regard to the angular orientation of each quadrant or other suitable data. In this exemplary embodiment, features having predetermined image parameters can be located using suitable image data analysis processes that do not require the angular orientation of the features within the image data to be known.

Feature inspection system 306 receives feature image data from feature identification system 304 and performs feature inspection, component inspection, or other suitable inspections. In one exemplary embodiment, feature inspection system 306 can receive the image data directly and can analyze the image data to locate defects, such as where the defects have a known size, shape, color density, pixel brightness characteristic, or suitable parameters that allow feature inspection to be performed without previously identifying die perimeters, individual features within the die, or other suitable elements. Likewise, feature inspection system 306 can receive component image data from feature identification system 304, die identification system 302, or other suitable systems, and can perform feature inspection based on previously-located die perimeters, components, or other suitable data. Likewise, other suitable processes can also or alternatively be used.

In operation, system 300 performs analysis and inspection of components and features using image data generated in conjunction with a rotating prism. System 300 allows quadrants or other suitable sections of components, such as dies, to be inspected, such as by identifying outlines of the die or other components that are being inspected, by identifying features within the die, by identifying damaged areas, either with or without adjusting for the angular orientation of the features, or in other suitable manners.

Figure 4:
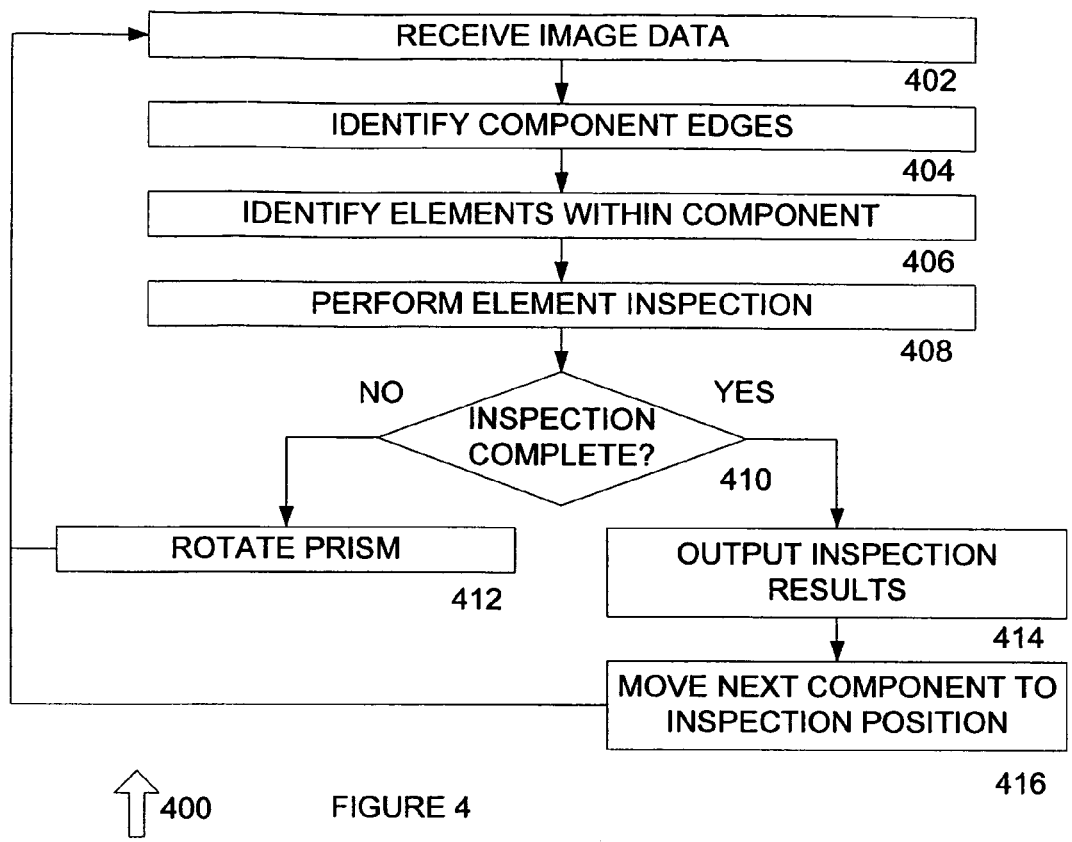
FIG. 4 is a flowchart of a method for performing an inspection using a rotating prism in accordance with an exemplary embodiment of the present invention.

FIG. 4 is a flowchart of a method 400 for performing an inspection using a rotating prism in accordance with an exemplary embodiment of the present invention. Method 400 begins at 402 where image data is received. In one exemplary embodiment, the image data can be received through a prism or other suitable devices that convey image data from a first area to a viewing area, such that rotation of the prism or other device will allow a larger field of view to be encompassed at the viewing area than would be encompassed directly from the viewing area with a predetermined pixel density and a predetermined pixel array size. The method then proceeds to 404.

At 404 component edges are identified. In one exemplary embodiment, image data analysis can first require identification of component edges, such as die edges or suitable data that is used to align the image data. Likewise, if component image data is not required, then the method can proceed directly to 406.

At 406 features within the component are identified. In one exemplary embodiment, the features can be identified based on a predetermined relationship of the features to one or more edges, based on known elements of the feature that allow the feature to be identified without previously identifying the component edges or the angular orientation of the component or section of the component being analyzed, or in other suitable manners. Likewise, if identification of features within the component is not required, such as where defect identification can be performed based on known image data characteristics of defects, the method can proceed directly to 408.

At 408 feature inspection is performed. In one exemplary embodiment, the features can be inspected after correcting for angular rotation, after locating the features relative to an edge, or in other suitable manners. In another exemplary embodiment, feature inspection can be performed by processing the image data to locate defects based upon known image data characteristics of such defects. Likewise, a suitable combination of processes can be used. The method then proceeds to 410.

At 410 it is determined whether the inspection is complete, such as whether all quadrants of a die have been inspected, whether all features or components have been inspected, or whether additional image data is required. If the inspection is not complete then the method proceeds to 412 where the prism or other device is rotated. In one exemplary embodiment, the prism can be rotated through four quadrants so as to generate an image of an entire semiconductor die. Likewise, other prism rotation angles can be used, all image data can be generated prior to performing element inspection such that prism rotation is not required, or other suitable procedures can be used. The method then returns 402.

If it is determined at 410 that inspection is complete the method proceeds to 414 where the inspection results are output. In one exemplary embodiment, the inspection results can include a pass/fail indicator as to whether or not the component should be accepted or rejected, such as control data that causes a failed component to marked or removed. Likewise, additional indicators can be provided, such as notification data that additional operator review is required or other suitable data. The method then proceeds to 416.

At 416 the next component is moved to the inspection position. For example, the components can be on a movable support such that the next component can be moved into the inspection position by moving the support. Likewise, the camera can be on a movable support such that the camera is moved to the next component, or other suitable processes can be used. The method then returns to 402.

In operation, method 400 is used to inspect components using a rotating prism or other suitable devices that allow the viewing area to be changed without moving the component, the camera, or otherwise taking actions that delay the inspection process. Method 400 can thus be used to increase the inspection speed, such as where moving the camera or component requires more time than rotation of a prism or other suitable devices.

Figure 5:
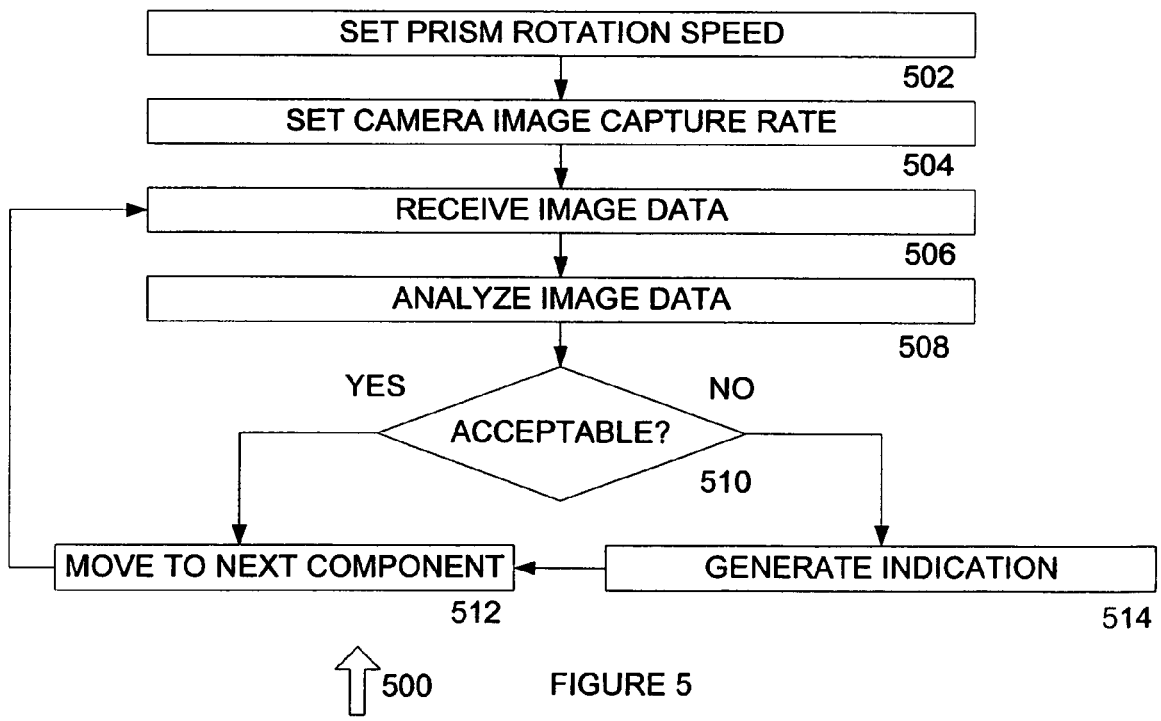
FIG. 5 is a flowchart of a method for inspecting components in accordance with an exemplary embodiment of the present invention.

FIG. 5 is a flowchart of a method 500 for inspecting components in accordance with an exemplary embodiment of the present invention. Method 500 begins at 502 where the prism rotation speed or other suitable device rotation speed is set. In one exemplary embodiment, the prism rotation speed can be set based upon a maximum data generation rate of an image data device, camera or other suitable devices. Likewise, where the rotation speed is fixed, the method can proceed directly to 504.

At 504 the camera image capture rate is set. In one exemplary embodiment, the camera image capture rate can be adjusted based on the rotation speed of the prism, can be calibrated or set to a predetermined rate, or other suitable processes can be used to set the image capture rate. The method then proceeds to 506.

At 506 image data is received. The image data can include two or more sets of image data that encompass one or more components. In one exemplary embodiment, a separate set of image data can be generated in sequence for each of four quadrants of a single die as a rotating prism rotates through each of the quadrants, and can be received at 506. In another exemplary embodiment, where an entire semiconductor wafer has been cut into dies and is being inspected, a suitable number of image data sets can be generated to cover all dies. Likewise, other suitable processes can be used. The method then proceeds to 508.

At 508, image data is analyzed. In one exemplary embodiment, image data is analyzed by first locating edges of a die or component, then by locating features within the image data relative to the edges, and then by inspecting each component individually. Likewise, the image data can be analyzed by looking for predetermined defect identifiers in the image data sets, by identifying components based upon known component image data relationships without correcting for angular displacement, or in other suitable manners. The method then proceeds to 510.

At 510 it is determined whether the image data is acceptable. If it is determined at 510 that the image data is acceptable, the method proceeds to 512 where the next component is moved into position. In one exemplary embodiment, a component support can be moved, the camera can be moved, or other suitable processes can be used. The method then returns to 506.

If it is determined at 510 that the image data is not acceptable, the method proceeds to 514 where indication data is generated. In one exemplary embodiment, the indication data can be a pass/fail indication, an indication that the component should be manually inspected, or other suitable indication data. The method then proceeds to 512 where the next component is moved into place. Likewise, the questionable or defective component can be removed, such as by using a pick and place tool or other suitable devices.

In operation, method 500 allows component inspections to be performed using a rotating prism or other suitable devices, so as to increase the inspection area for inspections performed at a given pixel density without requiring the camera or component to be moved. Method 500 further allows the angular displacement for such sets of image data to be compensated for.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. An inspection system comprising:
    a prism having a first end and a second end, where an inspection item is placed a predetermined distance from the first end of the prism and the second end provides an image of the inspection item; and
    an image data system disposed at the second end of the prism, the image data system generating two or more sets of two-dimensional image data of different surface areas of the inspection item.

2. The system of claim 1 further comprising an area inspection system coupled to the image data system, the area inspection system receiving two-dimensional image data from one of a plurality of areas of a field of view area.

3. The system of claim 1 further comprising a prism rotation controller coupled to the prism, the prism rotation controller setting a rotation speed of the prism.

4. The system of claim 1 further comprising an image data acquisition control coupled to the image data system, the image data acquisition control setting an image capture rate.

5. The system of claim 1 further comprising an area analysis system receiving the image data and generating inspection item area image data.

6. The system of claim 1 further comprising an inspection item identification system receiving the image data and generating inspection item image data.

7. The system of claim 1 further comprising a component identification system receiving the image data and generating component image data.

8. The system of claim 1 further comprising a component inspection system receiving the image data and generating component pass/fail data.

9. The system of claim 1 wherein the image data system comprises means for generating two or more pixel arrays of image data from a prism within a field of view.

10. The system of claim 1 further comprising means for identifying component edges from image data generated by the prism.

11. The system of claim 1 further comprising means for setting an image capture rate.

12. A method for inspection comprising:
receiving image data of a first area of an inspection item from a prism;
generating first area two-dimensional image data using an electronic image data system;
receiving image data of a second area of the inspection item from the prism;
generating second area two-dimensional image data using the electronic image data system;
receiving image data of a third area of the inspection item from the prism;
generating third area two-dimensional image data using the electronic image data system;
receiving image data of a fourth area of the inspection item from the prism;
generating fourth area two-dimensional image data using the electronic image data system; and
wherein the inspection items is inspected using the first area image data, the second area image data, the third area image data, and the fourth area image data.

13. The method of claim 12 wherein the item is a semiconductor package.

14. The method of claim 12 wherein the first area image data corresponds to a first area of a semiconductor package, the second area image data corresponds to a second area of the semiconductor package, the third area image data corresponds to a third area of the semiconductor package, and a fourth area image data corresponds to a fourth area of the semiconductor package.

15. A method for inspecting components comprising:
receiving image data of a first area of an assembly from a prism;
generating first area two dimensional image data that includes a first section of the assembly using an electronic image data system;
receiving image data of a second area of the assembly from the prism;
generating second area two dimensional image data that includes a second section of the assembly using the electronic image data system.

16. The method of claim 15 wherein the first section and the second section are each areas of semiconductor packages, and the prism generates image data of different areas of the semiconductor packages.

17. The method of claim 15 further comprising generating a plurality of two-dimensional set of image data, each set including one of a plurality of areas of the assembly.

18. The method of claim 17 further comprising identifying different non-linear areas of the assembly in the image data.

19. The method of claim 15 further comprising analyzing the second area image data based on a predetermined angular relationship to the first area image data.

* * * * *

UNITED STATES PATENT AND TRADEMARK OFFICE
CERTIFICATE OF CORRECTION

PATENT NO. : 7,684,610 B2
APPLICATION NO. : 12/072468
DATED : March 23, 2010
INVENTOR(S) : Soon Wei Wong et al.

It is certified that error appears in the above-identified patent and that said Letters Patent is hereby corrected as shown below:

Title Page, Page 1, section (75) - Inventors - please change "Kundapura Paremeshwara Srinivas" to -- Kundapura Parameshwara Srinivas --;

Col. 10, line 17, please change "set" to -- sets --.

Signed and Sealed this

Eighteenth Day of May, 2010

David J. Kappos
*Director of the United States Patent and Trademark Office*